US00PP32902P2

(12) United States Plant Patent
Holtmaat

(10) Patent No.: US PP32,902 P2
(45) Date of Patent: Mar. 16, 2021

(54) ***RUDBECKIA* PLANT NAMED 'RUDLO175'**

(50) Latin Name: *Rudbeckia hirta*
Varietal Denomination: RUDLO175

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/873,137

(22) Filed: Feb. 7, 2020

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474, 428
CPC ..... A01H 5/02; A01H 5/00; A01H 6/14
See application file for complete search history.

(56) References Cited

PUBLICATIONS

AB Cultivars *Rudbeckia* 'Loving', retrieved on Jul. 30, 2020, retrieved from the Internet at https://www.ab-cultivars.com/?portfolio=rudbeckia-loving-smileyz, one page. (Year: 2020).*
Newey 2019 Catalogue Perennial Plugs and Liners, retrieved on Jul. 28, 2020, retrieved from the Internet at https://www.newey.com/wp-content/uploads/Newey-PPL-Catalogue-2019.pdf, pp. 1-6, 132, 233. (Year: 2019).*

* cited by examiner

*Primary Examiner* — June Hwu
(74) *Attorney, Agent, or Firm* — Penny J. Aguirre

(57) ABSTRACT

A new cultivar of *Rudbeckia* plant named 'RUDLO175' that is characterized by its short, well-branched plant habit, its strong stems, its very floriferous blooming habit, its long flowering period, its pleasant looking foliage that is green in color, and its ray florets that are grey-orange to grey-red in color with grey-purple to black bases.

2 Drawing Sheets

CROSS-REFERENCE TO A RELATED APPLICATION

This application is related to a European plant breeders' rights application filed on Sep. 4, 2018, application No. 2018/2262. There have been no offers for sale anywhere in the world prior to the effective filing date of this Application and no accessibility to one of ordinary skill in the art could have been derived from the printed plant breeder's rights documents.

Botanical classification: *Rudbeckia hirta.*

Variety denomination: 'RUDLO175'.

BACKGROUND OF THE INVENTION

The present invention relates to a new and distinct cultivar of *Rudbeckia hirta* and will hereafter by referred to by its cultivar name, 'RUDLO175'. The new cultivar is an herbaceous perennial grown for use as a landscape plant.

'RUDLO175' was derived from a breeding program in July of 2016 conducted by the Inventor at a nursery in Zuidwolde, The Netherlands. The objective of the breeding program was to select a new cultivars of *Rudbeckia* with floriferous blooming habits and compact plant habits.

'RUDLO175' was selected in July of 2017 by the Inventor from amongst seedlings in a trial field that had been planted with seed derived from open pollination of numerous unpatented and unnamed proprietary plants from the Inventor's breeding program. The exact parentage is therefore unknown.

Asexual propagation of the new cultivar was first accomplished under the direction of the Inventor by tissue culture using meristematic tissue in Heerhugowaard, The Netherlands in January of 2018. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to a website listing by AB-Cultivars (a company owned by the Inventor).

SUMMARY OF THE INVENTION

The following traits have been repeatedly observed and represent the characteristics of the new cultivar. These attributes in combination distinguish 'RUDLO175' as a unique cultivar of *Rudbeckia.*

1. 'RUDLO175' exhibits a short plant height.
2. 'RUDLO175' exhibits a well-branched plant habit.

3. 'RUDLO175' exhibits strong stems.
4. 'RUDLO175' exhibits a very floriferous blooming habit.
5. 'RUDLO175' exhibits a long flowering period.
6. 'RUDLO175' exhibits pleasant looking foliage that is green in color.
7. 'RUDLO175' exhibits inflorescences with ray florets that are grey-orange to grey-red in color with grey-purple to black bases.

'RUDLO175' can be compared to the *Rudbeckia* cultivars SMILEYZ® 'Chocolate' (not patented), and SMILEYZ® 'RUDHT37' ((U.S. Plant Pat. No. 30,657) SMILEYZ® 'Chocolate -' is similar to 'RUDLO175' in plant height and in having strong stems. SMILEYZ® 'Chocolate' differs from 'RUDLO175' in having an earlier blooming season, ray florets that are broader in width and are dark grey-orange to brown in color. SMILEYZ® 'RUDHT37' is similar to 'RUDLO175' in plant height. SMILEYZ® 'RUDHT37' differs from 'RUDLO175' in commencing bloom earlier in the blooming season and in having ray florets that are greyed-orange to greyed-orange on the lower half and yellow-orange on the upper half.

BRIEF DESCRIPTION OF THE DRAWINGS

The accompanying colored photographs illustrate the overall appearance and distinct characteristics of the new *Rudbeckia*. The photographs were taken of a 4-month-old plant of 'RUDLO175' as grown outdoors in a 19-cm container in Zuidwolde, The Netherlands.

The photograph in FIG. 1 is a side view of 'RUDLO175' in bloom.

Figure 1:
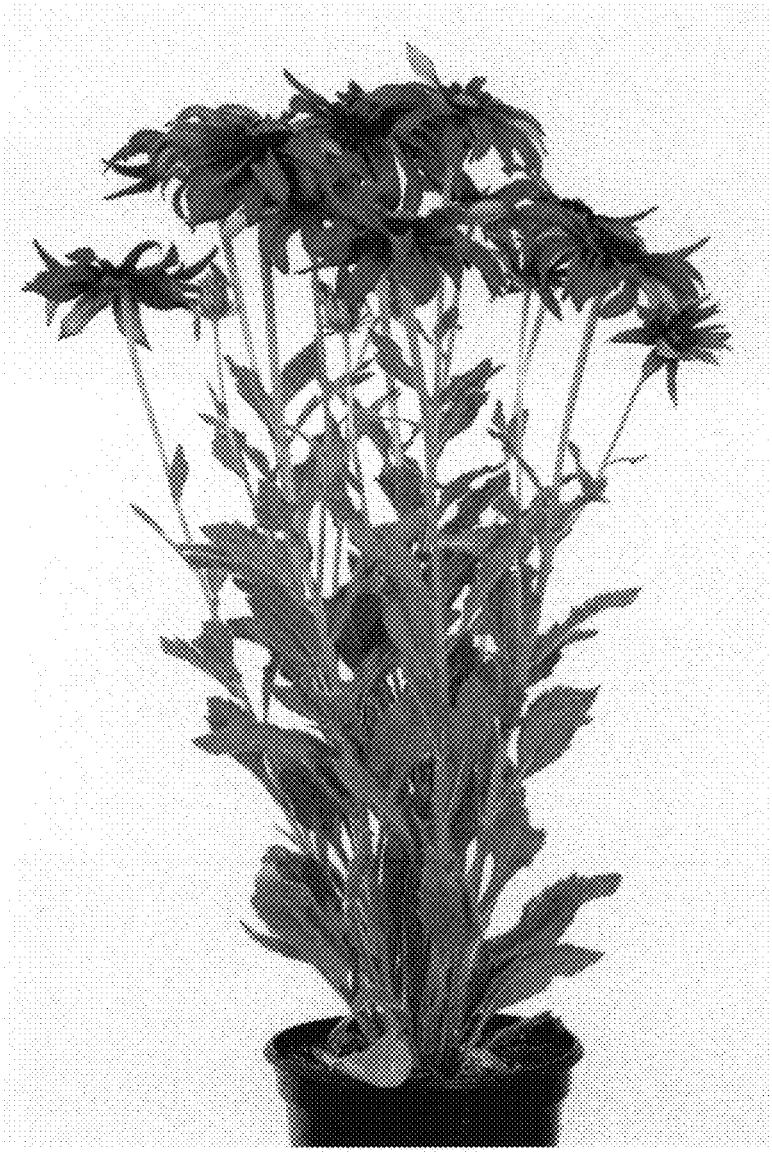
Figure 2:
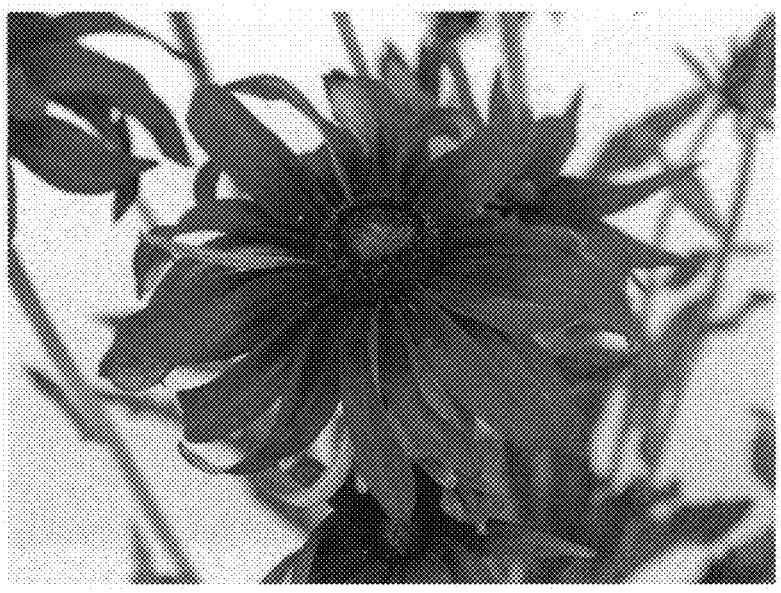

The photograph in FIG. 2 provides a close-up view of an inflorescences of 'RUDLO175'.

Figure 3:
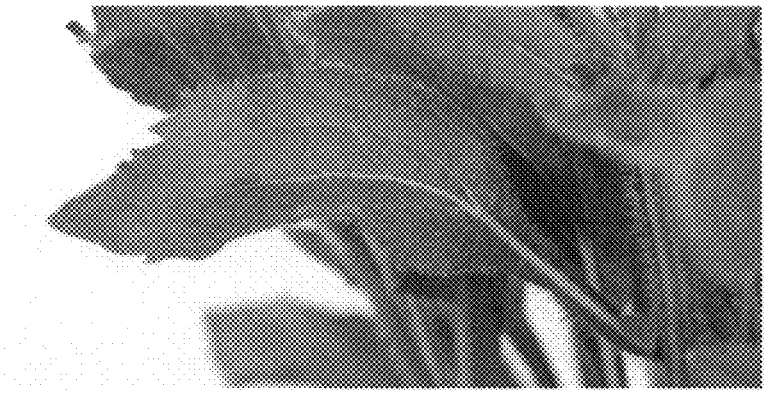

The photograph in FIG. 3 provides a close-up view of the foliage of 'RUDLO175'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 4-month-old plants of 'RUDLO175' as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Average of 13 weeks from early summer to late summer in The Netherlands.

*Plant type.*—Perennial.

*Plant habit.*—Broadly upright, compact.

*Plant shape.*—Obovate.

*Height and spread.*—Average of 48.5 cm in height from soil level to top of foliar plane and 66 cm in height from soil level to top of floral plane, 43.3 cm in diameter.

*Hardiness.*—At least in U.S.D.A. Zones 4 to 10.

*Diseases and pests.*—No susceptibility and resistance to diseases or pests has been observed.

*Root description.*—Fine and fibrous.

*Propagation.*—Tissue culture.

*Root development.*—An average of 3 weeks for root initiation with a young rooted plant produced in an average of 6 weeks.

*Growth rate and vigor.*—Vigorous.

Stem description:

*Shape.*—Moderately angled.

*Stem color.*—Young stems; 145A, mature stems; N144A, angles 144A, stems tinged at internodes 187C.

*Stem size.*—An average of 4 mm in diameter and an average of 29.1 cm in height.

*Stem surface.*—Moderately glossy and densely covered with strigose hairs an average of 2 mm in length and close to NN155D in color.

*Stem number.*—Average of 7 main stems, 1 lateral branch per main stem.

*Internode length.*—An average of 3.3 cm in length.

*Stem aspect.*—Main stems; average of 15° to vertical, lateral branches; average of 25° to main stems.

*Branching.*—Freely branching from base with lateral stems.

Foliage description (Cauline leaves):

*Leaf shape.*—Elliptic to ovate and obovate.

*Leaf division.*—Simple.

*Leaf base.*—Cuneate.

*Leaf apex.*—Acute.

*Leaf venation.*—Pinnate, color upper surface 145D, color lower surface 145A.

*Leaf margins.*—Coarsely serrate, coarsely moderately undulate.

*Leaf attachment.*—Petiolate.

*Leaf arrangement.*—Alternate.

*Leaf size.*—Average of 9.4 cm in length and 4.3 cm in width.

*Leaf color.*—Young upper surface; 143A, young lower surface; 147B to 147C, mature upper surface; 137A, mature lower surface; 137C.

*Leaf surface.*—Both surfaces rough to the touch, matte and densely pubescent with short strigose hairs; an average of 2 mm in length and NN155D in color.

*Petioles.*—Average of 3.9 cm in length, flattened, average of 7 mm in diameter at widest point and 3 mm in diameter at narrowest point, upper surface color; 145D, margins 137B, lower surface color; 144C and 144D, margins 137B, both surfaces slightly glossy and densely covered with strigose hairs; an average of 2 mm in length and 155A in color.

Foliage description (Basal leaves):

All characteristics match cauline leaves with the following characteristics differing: Arrangement; emerging from base, leaf size: 11 cm in length and 5 cm in width, leaf shape; obovate to ovate.

Flower description:

*Type.*—Terminal capitulum, consisting of ray florets and disk florets.

*Capitulum number.*—1 per stem, up to 16 per plant.

*Lastingness of inflorescence.*—Average of 2 weeks, persistent.

*Capitulum size.*—Matures to about 5.8 cm in height and 13.8 cm in diameter, disk size is an average of 2.8 cm in diameter.

*Fragrance.*—None.

*Involucral bracts* (*phyllaries*).—Broadly cuneate base, obtuse to bluntly acute apex, narrow oblong in shape, entire margins, average of 42 arranged in 3 rows, 2.1 cm in length and 3 mm in width, color; upper surface when fully open 137A, lower surface when fully open 143B and 143C, both surfaces matte and densely covered with strigose hairs; an average of 2 mm in length and NN155D in color.

*Receptacle.*—Broad ovate in shape, an average of 1.1 cm in height and 1.2 cm in diameter, 157C in color.

*Buds.*—Globular in shape, immature ray florets pointed upward and curling inward, up to 2.2 cm in length and 2.8 cm in diameter, immature ray florets between 4A and 154C in color, immature involucral bracts upper surface 143A in color, immature involucral bracts lower surface 143B, surface on involucral bracts and ray florets is densely covered with strigose hairs; an average of 2 mm in length, NN155D in color on bracts and 157A in color and adpressed on immature ray florets.

*Peduncle.*—Strong, straight on top of main flowering stem, average of 9.5 cm in length and 4.5 mm in diameter, color; 144A and axially striped 143A, surface moderately glossy sand densely covered with short strigose hairs; an average of 2 mm in length and NN155D in color.

*Ray florets.*—Average of 26 (varying between 22 and 28), rotate around the disk, oblong in shape, average of 7.2 cm in length and 2 cm in width, praemorse apex, cuneate base, entire margin, both surfaces are velvety, matte and glabrous, held near horizontal, color; when opening upper surface 175B, tinged 17B, veins 17C, when opening lower surface 152D to 153B, tinged 176B and 176C in the center, when fully opened upper surface a color between 175A and 183A, changing to a color between 187A and 203A at the base, veins 175C, when fully open lower surface 177B, flushed 153C towards the base, veins 153C to 153D.

*Disk flowers.*—Average about 900 slightly curved and tubular in shape, 20 whorls arranged spirally on a conical receptacle, lower 90% fused into tube, upper 10% free, tubular, about 8 mm in length and 4 mm in width, free lobes have entire margins, apices of free lobes acute, both surfaces glabrous and slightly glossy, color; when opening upper and lower surface 200A and 203A, mid-section 200A, base 155A, when fully open upper and lower surface 200A, mid-section 186A to 186B, base 155A, spines; none, bracts; 1 per disk floret, soft, flattened, an average of 7 mm in length and 1.5 mm in diameter, narrow cuneate in shape, acute apex, narrowly cuneate base, color; apex N186A, mid-section N186D, base 155A, matte surface and moderately pubescent with hairs; an average of 0.3 mm in length, N186C in color.

Reproductive organs:

*Gynoecium.*—Pistil; 1, 8 mm in length, style; 5 mm in length, color; top 200A, mid-section 155C, base 155C, stigma; cleft, decurrent, 5 mm in diameter, 200A in color, ovary; 155A in color.

*Androecium.*—Stamens; 5, filaments; 3 mm in length, 160D in color, anther; narrow oblong in shape, 2 mm in length, 0.5 mm in width, 200A in color, pollen; moderate in quantity and 17B in color.

*Fruit/seed.*—None observed to date.

It is claimed:

1. A new and distinct cultivar of *Rudbeckia* plant named 'RUDLO175' substantially as herein illustrated and described.

* * * * *